United States Patent
Cahill

(10) Patent No.: US 9,314,268 B2
(45) Date of Patent: *Apr. 19, 2016

(54) IMPLANT RECOVERY DEVICE

(71) Applicant: W.L. Gore & Associates, Inc., Flagstaff, AZ (US)

(72) Inventor: Ryan Cahill, Newtonville, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,404

(22) Filed: Jan. 12, 2015

(65) Prior Publication Data

US 2015/0127044 A1 May 7, 2015

Related U.S. Application Data

(63) Continuation of application No. 12/062,985, filed on Apr. 4, 2008, now Pat. No. 8,945,141.

(60) Provisional application No. 60/921,966, filed on Apr. 5, 2007.

(51) Int. Cl.
| | |
|---|---|
| *A61F 2/95* | (2013.01) |
| *A61B 17/34* | (2006.01) |
| *A61B 17/50* | (2006.01) |
| *A61B 17/00* | (2006.01) |
| *A61B 17/12* | (2006.01) |
| *A61M 25/06* | (2006.01) |

(52) U.S. Cl.
CPC ............. *A61B 17/3439* (2013.01); *A61B 17/50* (2013.01); *A61B 17/3468* (2013.01); *A61B 2017/00575* (2013.01); *A61B 2017/00592* (2013.01); *A61B 2017/00623* (2013.01); *A61B 2017/1205* (2013.01); *A61F 2002/9528* (2013.01); *A61M 25/0662* (2013.01)

(58) Field of Classification Search
CPC .......... A61B 17/3468; A61B 17/3439; A61B 2017/00623; A61B 2017/1205; A61F 2/95; A61F 2/962; A61F 2/966; A61F 2/97; A61F 2002/9528; A61F 2002/9534
See application file for complete search history.

(56) References Cited

U.S. PATENT DOCUMENTS

| | | | |
|---|---|---|---|
| 4,611,594 | A | 9/1986 | Grayhack et al. |
| 5,102,415 | A | 4/1992 | Guenther et al. |
| 5,370,647 | A | 12/1994 | Graber et al. |
| 5,464,408 | A | 11/1995 | Duc |
| 7,022,102 | B2 | 4/2006 | Paskar |
| 7,094,243 | B2 | 8/2006 | Mulholland et al. |
| 7,766,820 | B2 | 8/2010 | Core |
| 7,871,419 | B2 | 1/2011 | Devellian et al. |
| 7,963,952 | B2 | 6/2011 | Wright, Jr. et al. |
| 2004/0073230 | A1 | 4/2004 | Mulholland et al. |
| 2006/0122647 | A1 | 6/2006 | Callaghan et al. |

OTHER PUBLICATIONS

U.S. Appl. No. 60/847,755, filed Sep. 28, 2006, Forde et al.

*Primary Examiner* — Ashley Fishback
(74) *Attorney, Agent, or Firm* — DLA Piper LLP (US)

(57) ABSTRACT

The present invention provides a device for delivering and/or recovering an object, such as a patent foramen ovale (PFO) occluder. According to one embodiment of the invention, a device contains an outer sleeve and an inner sheath. The inner sheath has a proximal portion and a distal portion; the distal portion of the inner sheath is disposed inside the lumen of the outer sleeve. The distal portion of the inner sheath can expand radially to facilitate retrieval of an object. The distal portion of the inner sheath has a larger diametrical configuration than the proximal portion of the inner sheath. The distal portion of the inner sheath may be in the shape of a cone or similar shape. The distal portion of the inner sheath further includes slits that form flaps which collapse inward and overlap each other as the distal portion is in its unexpanded configuration.

4 Claims, 6 Drawing Sheets

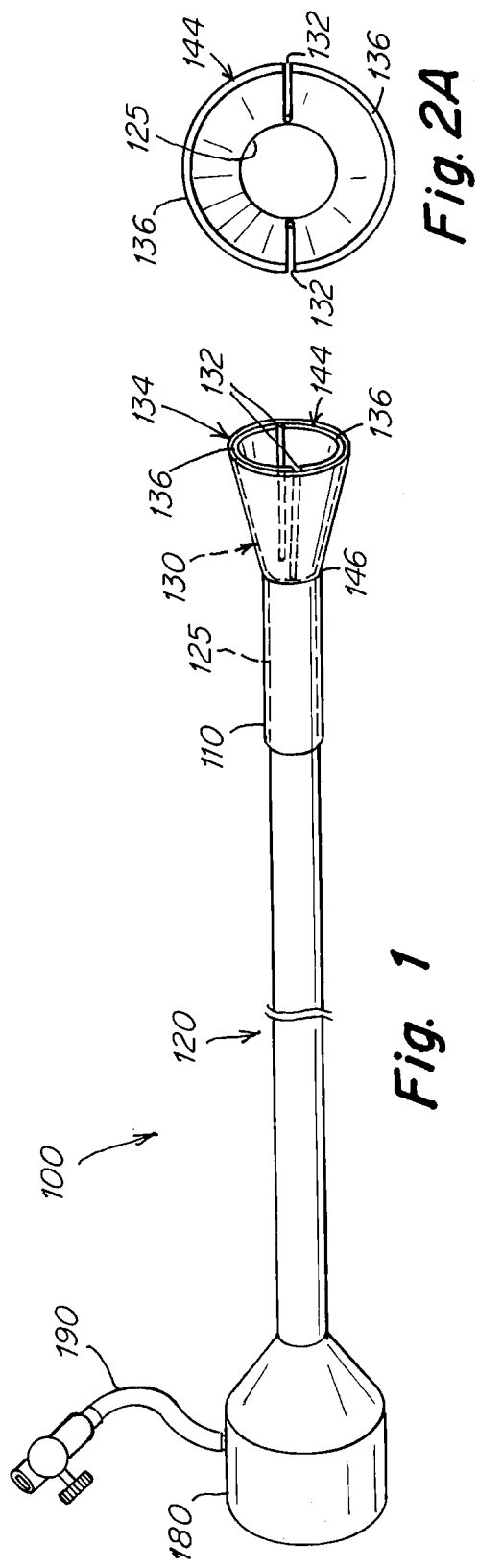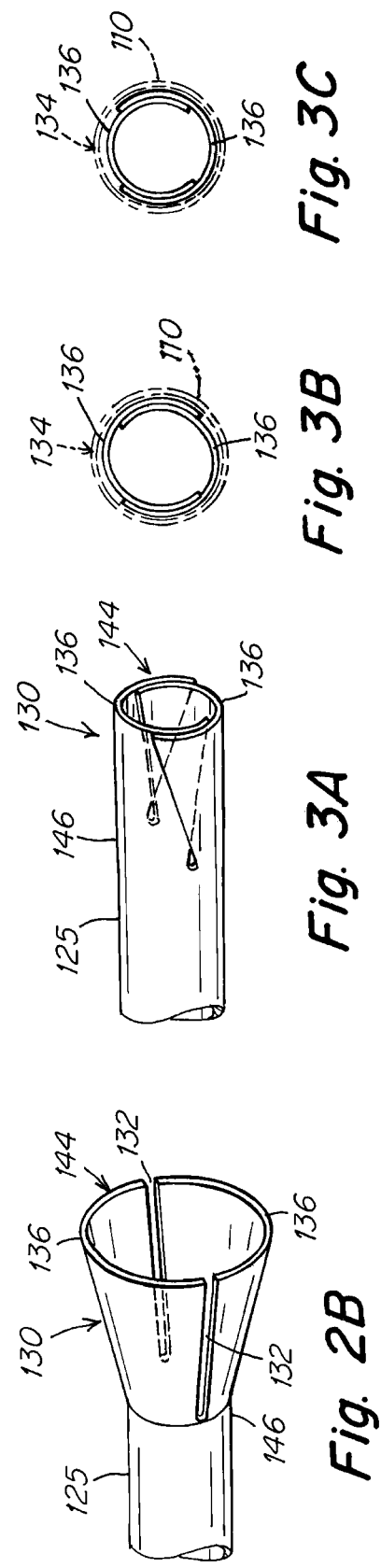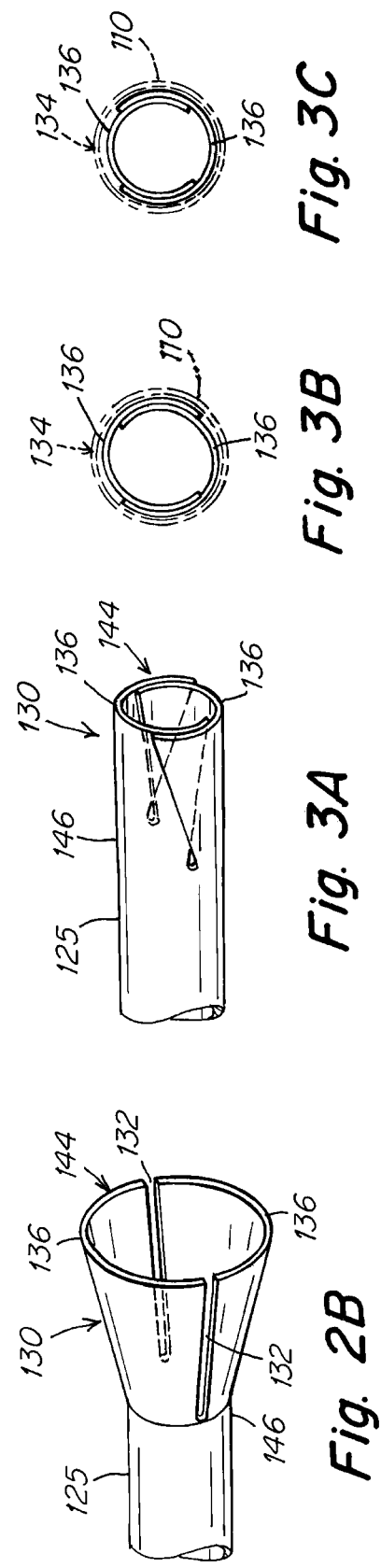

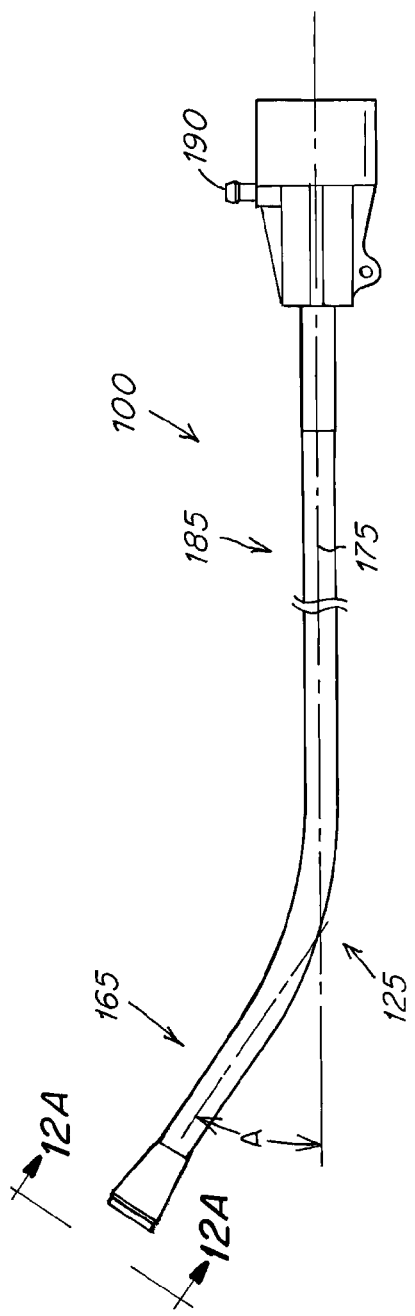
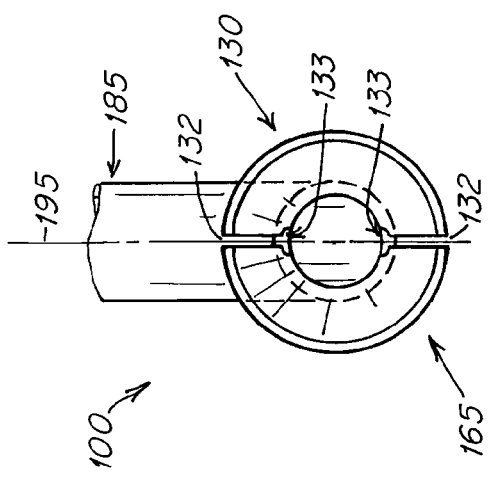
Fig. 12
Fig. 12A

IMPLANT RECOVERY DEVICE

CROSS-REFERENCE TO RELATED APPLICATIONS

This application is a continuation application of U.S. application Ser. No. 12/062,985 filed Apr. 4, 2004, now pending; which claims the benefit under 35 USC §119(e) to U.S. Application Ser. No. 60/921,966 filed Apr. 5, 2007. The disclosure of each of the prior applications is considered part of and is incorporated by reference in the disclosure of this application.

This application is related to U.S. Application Ser. No. 60/847,755, entitled Perforated Expandable Implant Recovery Sheath, filed Sep. 28, 2006; U.S. application Ser. No. 10/693,398, entitled Expandable Sheath Tubing, filed Oct. 24, 2004; and U.S. application Ser. No. 10/921,484, entitled Expandable Sheath Tubing, filed Aug. 19, 2004, which have the same assignee as the present invention and are incorporated herein by reference.

BACKGROUND OF THE INVENTION

1. Field of the Invention

The inventions relate to a sheath or catheter that has an expandable distal end.

2. Background Information

In many minimally invasive medical procedures, a sheath may be placed in a blood vessel to gain access to a site within a body for a diagnostic or therapeutic procedure. Sheaths and catheters are used as conduits to pass objects, such as surgical instruments, medical implants, or biological matter e.g., clots, tissue samples, or other matter. It is generally desirable to minimize the outer diameter of the sheath and maximize its inner diameter. A small outer diameter is desired to minimize the size of the wound at the insertion site. A smaller outer diameter also provides less disruption to the circulatory pathway. Within the constraint of the desired small outer diameter, the inner diameter of the sheath is designed to be as large as possible for the objects to pass through it. Since the outer diameter is preferably minimized and the inner diameter is preferably maximized, the wall of the sheath is relatively thin. The thin wall of the sheath can in some cases lack sufficient strength for insertion into a blood vessel or other circumstances in which the sheath may be subjected to longitudinal or circumferential forces. Thus, materials commonly selected for the construction of sheaths typically have high stiffness or rigidity.

Objects, such as surgical instruments, medical implants, or biological matter may require removal from the body or repositioning within the body. An object that is to be removed may be a temporary implant which has performed the desired diagnostic or therapeutic function. Alternatively, an object may be a permanent implant that requires removal for some other reason. Sometimes objects need to be repositioned in the body after their implantation. One way of retrieving the object for removal or repositioning is to pull the object back into a sheath (or push the sheath around the object) so that the object is disposed within the sheath. Once retrieved into the sheath, the object can be repositioned and redeployed at a desired delivery location, or removed completely from the body. Some objects have different delivery and deployed configurations. Objects that have an enlarged deployed configuration must be compressed or transformed to a reduced profile configuration in order to be reintroduced into a sheath.

In some cases, such an object may not collapse into its reduced profile configuration completely. In other cases, the object may have physical features or unique geometries, e.g., edges, protruding arms, etc. that require careful orientation and manipulation during removal or a repositioning procedure. These features can cause difficulty in retrieving such an object back into the sheath. Furthermore, this difficulty may be compounded by the material choice for and construction of the sheath. The high stiffness or rigidity of the sheath material may make the withdrawal of an object more difficult because such sheath will not expand to accommodate an object that cannot be completely reconstrained to its original reduced profile. The thin wall of such a sheath may lack sufficient strength and, therefore, may kink, bend or fold as an object is pulled into the distal end of the sheath. Moreover, the physical features or unique geometries of an object may be caught by the distal edge of the sheath, thereby dragging the edge inward and tearing the sheath or folding the sheath inward. This can result in an even smaller inner diameter and, therefore, increased difficulty of retrieving.

SUMMARY OF THE INVENTION

The invention provides methods and systems for delivering and recovering implant devices.

In one aspect of the invention, a device for delivering or retrieving an object from a site within the body includes an outer sleeve having a lumen and an inner sheath. The inner sheath has a proximal portion and a distal portion. The distal portion is disposed within the lumen; the distal portion has an unexpanded configuration and an expanded configuration; and the distal portion has a first distal inner diameter and a second proximal inner diameter. The first distal inner diameter is larger than the second proximal inner diameter when in the expanded configuration.

In another aspect of the invention, the distal portion of the inner sheath includes at least two axial slits extending proximally from a distal end of the distal end portion. The slits can optionally form flaps that collapse inward and overlap each other when the distal end portion is in the unexpanded configuration.

In a further aspect of the invention, a proximal end of each of the slits terminates in an end for reducing stress imposed on the inner sheath due to moving from the unexpanded configuration to the expanded configuration.

In yet another aspect of the invention, a side port defines a passage through a wall of the inner sheath for accessing a lumen of the inner sheath. The inner sheath has a circumference, and the passage of the side port and at least one of the slits are aligned within 20 degrees along the circumference of the inner sheath.

In one aspect of the invention, the device has a curved proximal portion. Optionally, at least one of the slits and the direction of the curve of the curved portion are aligned within 20 degrees relative to the direction of the curve.

In yet another aspect of the invention, the distal portion further includes a distal end, a proximal end, and a joint disposed between the distal end and the proximal end. The joint enables at least a part of the distal portion to deflect inward or outward relative to a central axis of the distal portion.

In a further aspect of the invention, a method of retrieving an object from a site within the body includes engaging the object with a retrieval system and withdrawing the object proximally toward a sheath system. The sheath system includes an outer sleeve having a lumen and an inner sheath. The inner sheath has a proximal portion and a distal portion. The distal portion is disposed within the lumen; the distal portion has an unexpanded configuration and an expanded configuration; and the distal portion has a first distal inner diameter and a second proximal inner diameter. The first distal inner diameter is larger than the second proximal inner diameter when in the expanded configuration. The method further includes contacting a distal edge of the distal portion with the object and applying a withdrawing force on the object in the proximal direction so that the distal portion of the inner sheath slides over the object. The method also includes pulling the object past the distal edge of the inner sheath and into the distal end portion.

These and other features and advantages will become apparent from the drawings and detailed description.

BRIEF DESCRIPTION OF THE DRAWINGS

FIG. 1 is a perspective view of a sheath system according to one embodiment of the invention.

FIG. 2A is an end view of the distal end of the inner sheath according to one embodiment of the invention.

FIG. 2B is a perspective view of the distal portion of the inner sheath according to one embodiment of the invention.

FIG. 3A is a perspective view of a distal portion of the inner sheath according to one embodiment of the invention.

FIGS. 3B and 3C are end views of the distal end of the inner sheath according to the embodiment of FIG. 3A.

FIG. 12 is a side view of a sheath system having a curved portion according to one embodiment of the invention.

FIG. 12A is an end view of the sheath system of FIG. 12.

DETAILED DESCRIPTION OF THE INVENTION

Figure 4:
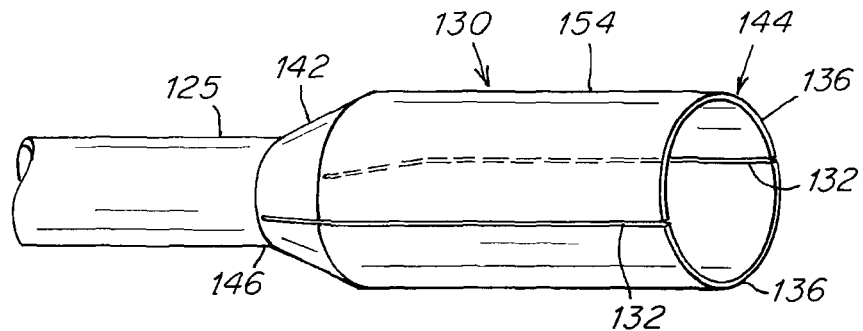
FIG. 4 is a perspective view of a distal portion of the inner sheath according to one embodiment of the invention.

Embodiments of the invention provide a sheath system that is suitable for constraining or reconstraining objects, such as surgical instruments, medical implants, or biological matter, e.g., clots, tissue samples, or other matter, so that they may be contained within the sheath during delivery, retrieval, or a repositioning procedure. Although embodiments of the invention are described as a sheath, a catheter can also incorporate aspects of the invention disclosed herein. In some cases, the terms sheath and catheter are used interchangeably. In this application, "distal" refers to the direction away from a sheath insertion location and "proximal" refers to the direction nearer the insertion location. According to some embodiments of the invention, a sheath system has a proximal portion with a first inner diameter and a distal portion with a different inner profile. In one embodiment of the invention, the distal portion of the sheath system can expand radially to accommodate an object with a larger profile than the distal portion of the sheath system. In other embodiments of the invention, the distal portion of the sheath system can expand radially to accommodate an object having an irregular shape or to accommodate a problematic orientation of the object as it enters the distal end of the sheath system. According to some embodiments, the sheath system is configured to facilitate the entry of an object and to further constrain the object into a smaller profile. In other embodiments, the sheath is configured to reduce the possibility of the object being caught on the distal end of the sheath, and, therefore, embodiments described herein reduce the possibility of the object snagging or tearing the sheath system.

The sheath system can be an introducer through which objects, such as surgical instruments, medical implants, e.g., stents, filters, occluders, or other devices, are inserted into a living body. The sheath system can also be a retriever through which objects, such as surgical instruments, medical implants, or biological matter, e.g., clots, tissue samples, or other matter, are withdrawn from a living body. In one aspect, the invention provides a sheath system suitable both for delivering an object and retrieving the same. In another aspect, the invention provides a recovery sheath system to accommodate the entry of an irregularly shaped object or to orient the object at its distal end to facilitate withdrawal of the object into the sheath system while providing sufficient column strength to reconstrain the object into a smaller profile. These aspects increase the ease of retrieval and provide for increased structural integrity, particularly when the object is contained within the sheath system. In another aspect, the invention provides a recovery sheath system with a reduced risk of splitting or tearing when an irregularly shaped object enters its distal end or reorients the object for withdrawal into the sheath system.

In some embodiments, a sheath system for deploying and/or recovering an object includes an outer sleeve and an inner sheath. The outer sleeve is disposed outside of the distal portion of the inner sheath. In some embodiments, a portion of the inner sheath is bonded to a portion of the outer sleeve, for example, thermally or by an adhesive. In some embodiments, the distal portion of the inner sheath has a radial dimension approximately equal to or slightly larger than the diameter of the proximal portion of the inner sheath. In various embodiments, the distal portion of the inner sheath may expand radially. In its expanded configuration, the diameter of the distal portion of the inner sheath increases gradually from the proximal end of the distal portion to the distal end of the distal portion of the inner sheath (or along a portion thereof). In various exemplary embodiments, the expanded distal portion of the inner sheath may have a cone shape, a bell shape, or a trumpet shape.

In some embodiments, the distal portion of the inner sheath may have one or more slits, which form flaps. In some embodiments, these slits can be present along a portion or the entire length of the distal portion of the inner sheath. In some embodiments, a portion of the areas of the flaps of the distal portion of the inner sheath that are adjacent to the slits overlap when the distal portion of the inner sheath is in an unexpanded configuration. In a radially expanded configuration, both the radial dimension of the distal portion of the inner sheath and the outer sleeve are expanded to facilitate retrieval of the device.

In one embodiment of the invention, the distal portion of the inner sheath having slits, described herein, may be used together with other formations, e.g., perforations, hinges, etc. to allow for further radial expansion as the object is being positioned within the distal portion of the inner sheath. In some embodiments of the invention, other materials can be added to the distal portion of the inner sheath, such as metal wires for enhancing strength, coatings to change friction characteristics, surface treatment to achieve a different durometer, and/or marker bands to attain radiopacity.

It is desirable that an expandable distal portion of a sheath system accommodate an object with a larger dimension than that of the inner dimension of the proximal portion of the sheath system. A sheath system with a radially expandable distal portion functions as a delivery conduit for objects to position and deploy the objects at a treatment site. A radially expandable distal portion of a sheath system also allows objects, including such objects as may be folded, compressed, or loaded in the sheath in a specialized manner, to be retrieved into a smaller diameter proximal portion of the sheath than otherwise possible. The expandable distal portion of the sheath system can more easily accommodate the volume of a partially or wholly deployed object, and can overcome snags that would otherwise result from the geometry of a partially or wholly deployed object, thereby reducing trauma to the blood vessel during the retrieval and repositioning procedure.

Referring to the drawings, wherein like reference numerals designate identical or corresponding parts throughout the several views, and more particularly to FIG. 1 thereof, a sheath system 100 is illustrated. Sheath system 100 has an outer sleeve 110 and an inner sheath 120. The inner sheath 120 includes a proximal portion 125 and a distal portion 130. In the figure, distal portion 130 is shown in an expanded configuration for the purposes of illustration, to differentiate the distal portion 130 from the proximal portion 125. In the expanded configuration, distal portion 130 has a relatively larger diameter at a distal end 134 of distal portion 130 and a relatively smaller diameter at a proximal end 146 of the distal portion 130. However, as explained in greater detail below, the distal portion 130 typically remains in an unexpanded configuration until an object is drawn into the distal portion 130 of the sheath system 100, thereby causing the distal portion 130 to expand. Herein, the words "constrained", "contained", and "collapsed" are also used to describe the unexpanded configuration of the distal portion 130. In addition, the words "unconstrained" and "uncontained" are also used to described the expanded configuration of the distal portion 130. However, it is understood that in preferred embodiments, the state of the distal portion when ready for use is the unexpanded configuration.

In some embodiments, as shown in FIG. 1, the outer sleeve 110 is disposed outside a portion of the proximal portion 125 and a portion of the distal portion 130 of the inner sheath 120. In other embodiments, the outer sleeve 110 may be substantially limited to the distal portion 130 with only a short proximal extension over a portion of the proximal portion 125 of the inner sheath 120. In such an embodiment, outer sleeve terminates close to the proximal end 146 of distal portion 130. Outer sleeve 110 provides a smooth outer surface, adds column strength to the sheath system 100, and contains at least a portion of distal portion 130.

The outer sleeve 110 and distal portion 130 of the inner sheath 120 may optionally be bonded together, for example, thermally or by an adhesive. In some embodiments, the proximal end of the outer sleeve 110 is bonded to the inner sheath 120 along the entire circumference of the proximal portion 125 that the outer sleeve 110 surrounds. In other implementations, portions of the outer sleeve 110 are bonded to portions of the inner sheath 120 in a longitudinal fashion from a location near the proximal end 146 of the outer sleeve 110 to a location near the distal end 134 of the outer sleeve 110. In other words, longitudinal strips of the outer sleeve 110 are bonded to underlying longitudinal strips of the inner sheath 120.

In further embodiments, partial circumferential bonding is used to bond portions of the outer sleeve 110 to the inner sheath 120. For example, the portion of the outer sleeve 110 overlying the distal portion 130 of the inner sheath 120 is circumferentially bonded along part of the circumference of the distal portion 130, but not in the distal portion 130 where slits 132 are present or where sections of the distal portion 130 overlap (described below). In yet further embodiments of the invention, the outer sleeve 110 and distal portion 130 of the inner sheath 120 may be bonded together by the elasticity of the outer sleeve 110. According to still further embodiments of the invention, the outer sleeve 110 is elastic to permit expansion of the distal portion 130 of the inner sheath 120.

In some embodiments, the distal end of the outer sleeve 110 extends further distally than the distal end 134 of the distal portion 130 of the inner sheath 120, i.e., beyond the distal end 134 of the distal portion 130 of the inner sheath 120, forming a small overhang or lip. One advantage of this lip is that it further prevents snagging upon entry of an object. In some implementations of this embodiment, the construction of the outer sleeve 110 is thin and highly flexible. Thus, the lip portion of the outer sleeve 110 easily deforms inwardly when it snags on an object as the object is being withdrawn into the distal portion 130 of inner sheath 120. In addition, the lip serves to self-center certain objects as the objects are being withdrawn into the distal portion 130 of inner sheath 120, as described in greater detail below.

In a preferred embodiment, the thickness of the outer sleeve 110 is tapered at the distal end to form a thin edge. This provides an ease of entry and transition as the sheath system 100 is inserted through the vasculature. According to some embodiments of the invention, the sheath system 100 can be used to deliver, retrieve, reposition and/or remove an object such as surgical instruments, medical implants, and/or biological matter. The sheath system 100 according to this embodiment is adapted to be introduced through the vasculature in a normal procedure as known to those skilled in the art. During delivery, an object is introduced from the proximal end 180 to the distal end 134 of the sheath system 100 and placed into a patient. When the sheath system 100 is used to remove or reposition an object, the object enters the sheath system 100 at its distal end 134.

According to some embodiments of the invention, as illustrated in detail views (wherein outer sleeve 110 is omitted) in FIGS. 2B, 4-8B, the distal portion 130 of the inner sheath 120 has a radially expanded configuration, with a larger diameter than the proximal portion 125 of the inner sheath 120. According to one embodiment, in its radially expanded configuration, the distal portion 130 of the inner sheath 120 has a first diameter at it distal end 144 and a second diameter at its proximal end 146, such that the first diameter is greater than the second diameter. According to some embodiments, the radially expanded configuration of the distal portion 130 of the inner sheath 120 could be in the shape of a cone, a bell, a funnel, a trumpet, or any other shapes that provide a greater distal circumference and a relatively smaller proximal circumference. In one embodiment of the invention, the graduated portion can be provided adjacent to the distal end 144 or more proximally. FIG. 4 illustrates a funnel-shaped, radially expanded, distal portion 130 with a tubular shaped segment 154 toward the distal end 144 of the distal portion 130 and a shorter, but more steeply angled, cone 142 toward the proximal end 146 of the distal portion 130. Although the outer sleeve 110 is omitted for clarity, it is understood that in an assembled sheath system, the outer sleeve 110 can cover all or a portion of the distal portion 130 of the inner sheath 120, as described above.

According to some embodiments, distal portion 130 includes slits, such as the two slits 132, extending from the distal end 144 to proximal end 146 of the distal portion 130 of the inner sheath 120, described further below. According to one embodiment of the invention, the slits 132 are straight. In an alternative embodiment, the slits could be curved, or zig-zagged, or any other suitable shape or configuration. In some embodiments, the radially expanded configuration could be formed by thermal-forming the distal portion of a regular sheath with the aid of a dye. In other embodiments, the radially expanded configuration could be made of any other means known to those skilled in the art.

Figure 6:
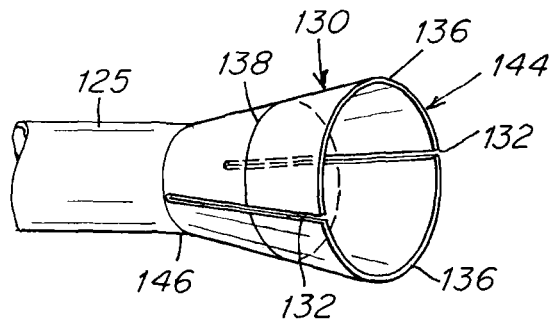
FIG. 6 is a perspective view of a distal portion of the inner sheath according to one embodiment of the invention.
Figure 7:
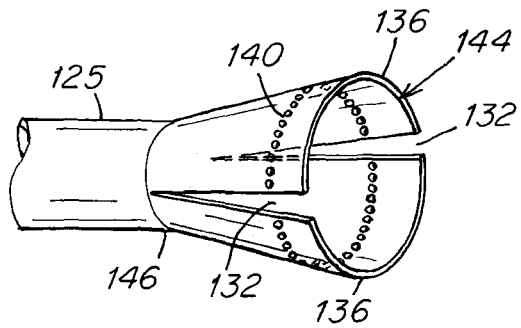
FIG. 7 is a perspective view of a distal portion of the inner sheath according to one embodiment of the invention.
Figure 8A:
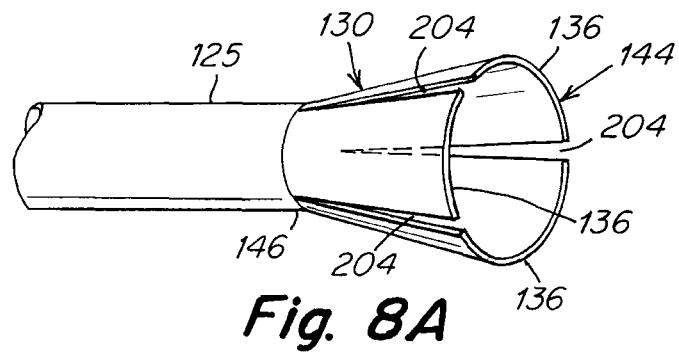
FIG. 8A is a perspective view of a distal portion of the inner sheath according to one embodiment of the invention.

With continuing reference to FIGS. 2A-B, and 4-7, the distal portion 130 of the inner sheath 120 contains two slits 132 extending from the distal end 144 to the proximal end 146 of the distal portion 130 of the inner sheath 120. In the illustrated embodiments in FIGS. 2B, 4-8B, the two slits 132 are disposed 180 degrees apart on opposite walls of the distal portion 130 of the inner sheath 120. The two slits 132 form two flaps or sections 136 in the distal portion 130 of the inner sheath 120. FIGS. 2A and 2B illustrate views of the distal portion 130 of the inner sheath 120 in a radially expanded configuration according to one embodiment of the invention. In other embodiments, the slits 132 could be disposed at different relative locations. In other embodiments, three, four or more slits could be provided, evenly spaced apart or spaced apart at different intervals. For example, FIG. 8A illustrates a conical distal portion 130 including three slits 204, spaced equally around the circumference of the distal end 144. It is contemplated that too many slits could potentially compromise the column strength of the distal portion 130 of the inner sheath 120, and, therefore, a high number of slits is not preferred. The slits 132 permit the distal portion 130 to further expand as needed.

Figure 8B:
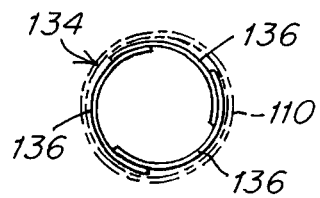
FIG. 8B is a front elevation view of the distal end of the inner sheath according to the embodiment of FIG. 7A.

As explained above, the distal portion 130 is typically in an unexpanded configuration. FIG. 3A shows a side perspective view of the distal portion 130 in the unexpanded configuration; outer sleeve 110 is omitted for clarity. FIG. 3A also shows flaps 136 defined by the slits 132. In the unexpanded configuration, flaps 136 collapse inward, and sections of the flaps 136 overlap each other. FIGS. 3B-C and 8B illustrate the distal end view of the distal portion 130 in the unexpanded configuration. In these figures, the outer sleeve 110 is shown in broken lines. As described above, portions of the distal portion 130 can be bonded to portions of the outer sleeve 110 using longitudinal and/or circumferential bonding. In embodiments having overlapping flaps 136, the outer sleeve 110 and the distal portion 130 are not bonded in the areas of the overlapping flaps 136 to enable free movement of the distal portion between the unexpanded and expanded configurations.

When the distal portion 130 of the inner sheath 120, disposed within the outer sleeve 110, is not expanded by the introduction of an object, the distal end 130 of the inner sheath 120 has a reduced profile approximately equal to that of the proximal portion 125. As shown in FIG. 3A, which is an unexpanded configuration, the flaps 136 of the distal portion 130 of the inner sheath 120 roll and fold inside one another, resulting in a smaller profile. The area of the flaps 136 adjacent to the slits 132 collapse inward and overlap each other. As shown in FIG. 3B, in one embodiment, one side of the first flap collapses inside the adjacent side of the second flap while the other side of the first flap folds outside the adjacent side of the second flap. As shown in FIG. 3C, in another embodiment, both sides of one flap collapse inside both sides of the other flap.

Thus, the outer sleeve 110 can, in some implementations, limit the degree to which flaps 136 separate when forced into an expanded configuration. Furthermore, the flexible nature of outer sleeve can assist in bringing flaps 136 back together into the unexpanded configuration after and object has been pulled through distal portion 130. According to one embodiment, the outer sleeve 110 is used to provide additional column strength for the sheath system 100 and to further constrain a retrieved object into a smaller profile. These features ease the transition of the object from distal portion 130 to proximal portion 125 of the inner sheath 120. The distal portion 130 of the inner sheath 120 can expand radially when an object having a diameter larger than the diameter of the proximal portion 125 of the inner sheath 120 is introduced at the distal end 144. Although not required, the outer sleeve 110 can be sized to prevent inner sheath 120 from expanding radially greater than a predetermined amount. For example, in a preferred embodiment, the outer sleeve 110 can prevent the distal portion 130 of the inner sheath 120 from expanding beyond a point which would cause an inner surface of the outer sleeve 110 to be exposed within the inner lumen of inner sheath 120. In this way, in those certain embodiments, the inner sheath 120 can prevent the inner surface of the outer sleeve 110 from coming into contact with an object that is to be withdrawn into the sheath system 100.

In some embodiments, the inner sheath can be made of polyether-polyamide block copolymer, such as resins sold under the Pebax® name (commercially available from Arkema, Inc.), high density polyethylene, polytetrafluoroethylene (PTFE), or perfluoro (ethylene-propylene) copolymer (FEP). In some embodiments, the durometer of the inner sheath is roughly around 20-70 on the SHORE D scale. According to some embodiments, the outer sleeve 110 can be made of any flexible material such as a styrene-ethylene-butadiene block copolymer (such as C-Flex®, commercially available from Consolidated Polymer Technologies, Inc., of Clearwater, Fla. or Kraton®, commercially available from Kraton Polymers, LLC, of Houston, Tex.), silicone, or polyurethane. It is generally desirable for the outer sleeve 110 to be made of a material with a durometer on a SHORE A scale of about 60-80. These ranges are only examples, and materials with other durometers could be used; for example, the material referred to as C-Flex® is commercially offered with a durometer of about 5-95 on the SHORE A scale.

According to one embodiment of the invention, as illustrated in FIG. 1, the sheath system comprises an inner sheath 120 and an outer sleeve 110 with the distal portion 130 of the inner sheath 120 disposed within the inner lumen of the outer sleeve 110. The sheath system 110 can be various lengths as suitable for a particular application, such as between 40 cm and 250 cm. The sheath system 110 can be longer or shorter as necessary for a particular application. The outer diameter of the sheath system 110, including inner sheath 120 at the proximal portion 125 and the unexpanded distal portion 130, is typically between 3 and 34 French. The sheath system 110 could have a larger or smaller diameter as a particular application warrants.

The length of the distal portion 130 of the inner sheath 120 can be adapted to the particular desired application. In some embodiments, the length of the distal portion 130 of the inner sheath 120 ranges from about 0.254 cm to about 5.08 cm. In a preferred embodiment, the length of the distal portion 130 of the inner sheath 120 is about 1.27 cm. The diameter of the distal end 144 of the inner sheath 120, at its radially expanded configuration, can be adapted to the particular desired application. In some embodiments, the diameter of the distal end 144 of the inner sheath 120 in its radially expanded configuration, and without the constraint of the outer sleeve 110 or further expansion provided by the slits, can be just slightly greater than the diameter of the proximal portion 125 to about 4 times the diameter of the proximal portion 125. In a preferred embodiment, the diameter of the distal end 144 of the inner sheath 120 in its radially expanded configuration, without the constraint of the outer sleeve 110 or further expansion provided by the slits, is about 2.25 times the diameter of the proximal portion 125. Typical wall thickness of the inner sheath 120 is between about 0.0127 cm and about 0.1905 cm. The wall thickness can vary greatly depending on the material selected and applications intended.

To further facilitate retrieval, the distal portion 130 of the inner sheath 120 can be modified to reduce the likelihood of an object being caught when the object is withdrawn into the inner sheath 120. In a preferred embodiment, a hinge is created near the distal end 144 of the distal portion 130 of the inner sheath 120. As an object enters the distal end 144 of the distal portion 130 of the inner sheath 120, the distal end 144 of the distal portion 130 of the inner sheath 120 bends outward (or inward) and, therefore, allows the object to slide smoothly into the distal portion 130 of the inner sheath 120. In other embodiments, referring to FIG. 6, a hinge 138 is created near the proximal end 146 of the distal portion 130 of the inner sheath 120. In some embodiments, the hinge 138 is created mid-way between the distal end 144 and the proximal end 146 of the distal portion 130 of the inner sheath 120. In other embodiments, a hinge is created nearer the distal end 144 of the distal portion 130 of the inner sheath 120, such as, for example, one-tenth to one-quarter of the total distance between the distal end 144 of the distal portion 130 and the proximal end 146 of the distal portion 130 of the inner sheath 120. In yet further embodiments, a hinge is created anywhere on the distal portion 130 of the inner sheath 120.

According to some embodiments, a hinge is created by treating the material so that a bend point is created. According to other embodiments, a hinge could also be created by perforation or by reducing the wall thickness of the inner sheath 120. FIG. 6 illustrates a hinge 138 created by a bending point around the circumference of the flaps 136. FIG. 7 illustrates a hinge 140 near the distal end 144 of the distal portion 130 of the inner sheath 120 created by small perforations around the circumference of the flaps 136.

Figure 5:
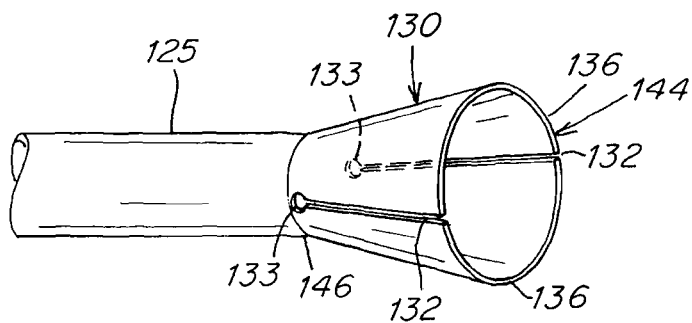
FIG. 5 is a perspective view of a distal portion of the inner sheath according to one embodiment of the invention.

In some embodiments, the slits 132 also have stress release ends. As shown in FIG. 5, distal portion 130 of the inner sheath 120 includes slits 132 and stress release ends 133 at the proximal end of the slits 132. This stress release ends 133 are created by removing additional material at the proximal end of the slits 132 as shown in FIG. 5, such as by drilling holes in distal portion 130. These stress release ends 133 facilitate the expansion of the distal portion 130 of the inner sheath 120 while avoiding any splitting, tearing, bending or other undesirable and unintentional deformations of the inner sheath 120 at the proximal end of the slits 132. In a preferred embodiment, the stress release ends 133 are located at the proximal end 146 of the distal portion 130 of the inner sheath 120. That is, the center points of the circular stress release end 133 fall on the transition from the proximal portion 125 to the distal portion 130. In other embodiments, the stress release ends 133 are located distal to the proximal end 146 of the distal portion 130 of the inner sheath 120.

Figure 9:
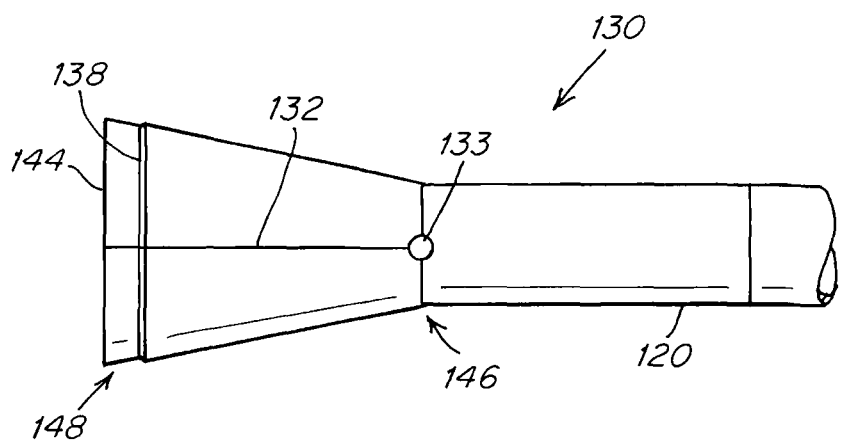
FIG. 9 is a side view of a distal portion of the inner sheath according to one embodiment of the invention.

FIG. 9 is a side view of a preferred embodiment of the distal portion 130 of the inner sheath 120 having one possible combination of the features described above. For the purposes of illustration, this embodiment is shown in the expanded configuration of the distal portion 130 of the inner sheath 120 and without outer sleeve 110. However, this embodiment can have an outer sleeve 110 with or without an overhanging lip distal to the distal end 144 of the inner sheath 120, as described above. The distal portion 130 has two slits 132 and two stress release ends 133 at the proximal end of the slits 132. The distal portion 130 also has a reduced thickness portion 148. The reduced thickness portion 148 extends from the distal end 144 to a hinge 138. In this embodiment, the reduced thickness portion 148 is about one-ninth the total length of the distal portion 130 of the inner sheath 120.

The following is a general description of how the various features in the embodiment shown in FIG. 9 cooperate to improve the snag-resistance of sheath system 100. FIGS. 10A-10D illustrate how one possible embodiment of the invention can be used to remove an object from a body. In FIGS. 10A-10D, the object is one example of a septal repair implant 200 (for example, a STARFlex® implant device available from NMT Medical, Inc.), having umbrella arms that expand when deployed. It is understood that the following is only one example of how embodiments of the invention may be used. Furthermore, the embodiments of the invention can be used to remove other objects from a living body, including, but not limited to, other types of repairs devices and other types of implant devices. Moreover, as described above, embodiments of the invention can be used to deploy or remove objects other than implant devices.

Referring to FIGS. 10A-10D, for the purposes of illustrations, only two umbrella arms of the implant 200 are shown (in line with the plane of the page), it being understood that implant 200 may have more than two arms, which can extend above and/or below the plane of the page. The embodiment of the sheath system 100 shown includes the features described in FIG. 9. In addition, sheath system 100 has an over-hanging lip portion 112, described above. Also for the purposes of illustration, only a central-cross section of the sheath system 100 is shown. Thus, although this embodiment has slits 132 and stress release ends 133, one slit 132 and stress release end 133 falls below the plane of the page, while the opposing slit 132 and stress release end 133 are above the plane of the page. Furthermore, the thickness of the outer sleeve 110 relative to the inner sheath 120 is not shown to scale. Likewise, the relative thickness of a distal end 144 of the inner sheath 120 distal to hinge 138 is not shown to scale.

Figure 10A:
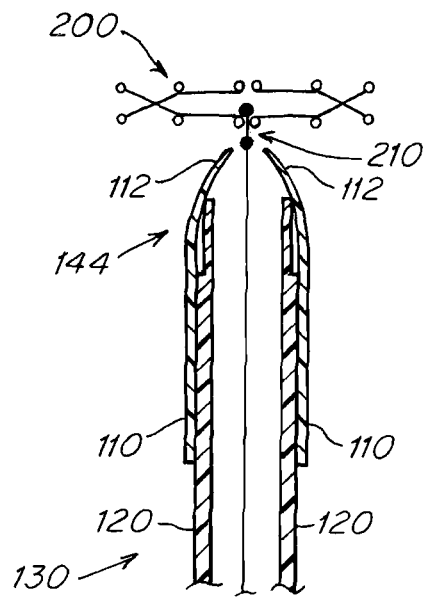
FIG. 10A-D is an illustration of an occluder being withdrawn into a distal portion of a sheath system according to one embodiment of the invention.
Figure 10B:
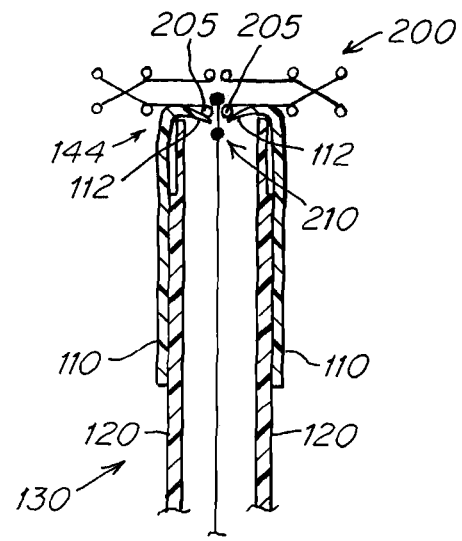

Referring now to FIG. 10A, the implant is engaged by a retrieval mechanism 210, for example, a snare retrieval system. Snare retrieval system 210 is shown schematically for simplicity, it being understood that the features of the retrieval system used to engage implant 200 may vary. The implant 200 is drawn proximally until shoulder coils 205 come into contact with an over-hanging lip portion 112 of outer sleeve 110. As the implant 200 is pulled proximally, the lip portion 112 folds inward and centers the implant 200 to better align it with the inner sheath 120 (as shown in FIG. 10B). The implant 200 is then pulled further proximally until the arms of the implant 200 come into contact with the distal end 144 of the inner sheath 120. Because only the central cross-section of the sheath system 100 and only two arms of implant 200 are shown, it appears that only two arms come into contact with lip portion 112 and distal end 144. However, as lip portion 112 and distal end 144 are circular, it is understood that more than two arms may come into contact with these features. Moreover, depending on the orientation and specific design of implant 200, the arms of implant 200 may come into contact with these features at different times during the retrieval procedure.

Figure 10C:
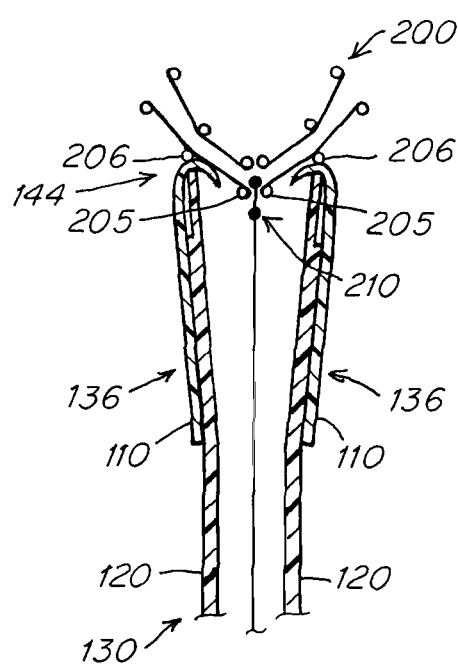

Referring to FIG. 10C, as further withdrawing force is applied to the implant 200, the flaps 136 slide against each other, and the distal portion 130 of the inner sheath 120 expands radially to accommodate the larger profile of the collapsing implant 200. Because only a cross-section of sheath system 100 is shown, only a cross-section of flaps 136 are shown. In addition, the slits 132 and the stress release ends 133 (not shown, as they lie out of the plane of the page) facilitate the radial expansion of the distal portion 130 of the inner sheath 120 and reduced the likelihood of splitting, tearing, bending or other undesirable and unintentional deformations of the inner sheath 120 at the proximal end of the slits 132. FIG. 10C shows that elbow coils 206 can become hung-up on the distal end 144 of the distal portion 130.

Figure 10D:
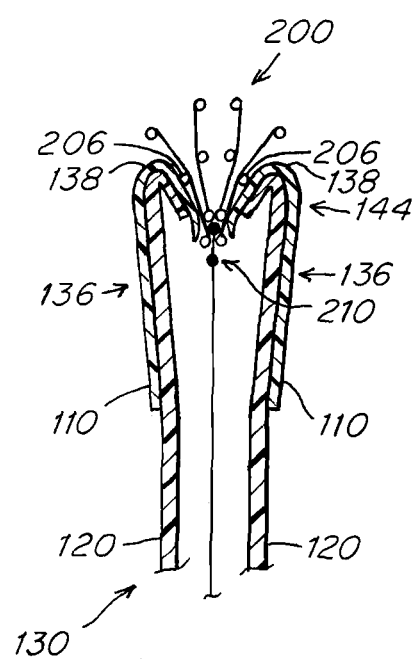

Referring now to FIG. 10D, as still further withdrawing force is applied to the implant 200, the hinge 138 of the inner sheath 120 enables the distal end 144 of the inner sheath 120 to bend inward and facilitate passage of the implant 200 into the inner lumen of inner sheath 120. In addition, as the implant 200 enters the distal portion 130 of the inner sheath 120, the funnel-shape created by the flaps 136 of the distal portion 130 compresses the implant 200 into a configuration to allow implant 200 to be drawn into the main portion of the sheath system 100. Although only a minimal amount of expansion is shown in FIGS. 10C-10D, it is understood that the distal portion 130 is capable of further expansion than that shown, and would expand further, as permitted by the particular features of this embodiment, as the implant 200 is withdrawn further into the distal portion 130. As the implant is withdrawn into the sheath system 100, proximal to distal portion 130, the distal portion 130 returns to its unexpanded configuration.

Referring again to FIG. 1, that figure shows an embodiment of sheath system 100 with a proximal side port 190 disposed on the proximal end 180 of the sheath system 100. The proximal side port 190 provides access to the inner lumen of inner sheath 120, which enables fluid such as saline or blood to enter or exit the inner sheath 120. In one embodiment, as illustrated in FIG. 1, the two slits 132 extending from distal end 144 of the inner sheath 120 are disposed 90° radially relative to the orientation of the proximal side port 190. In a preferred embodiment, as illustrated in FIG. 11, slits 132 are aligned radially with the proximal side port 190, such that both slits 132 and side port 190 fall in a plane passing along the center axis of the inner sheath 120.

Figure 11:
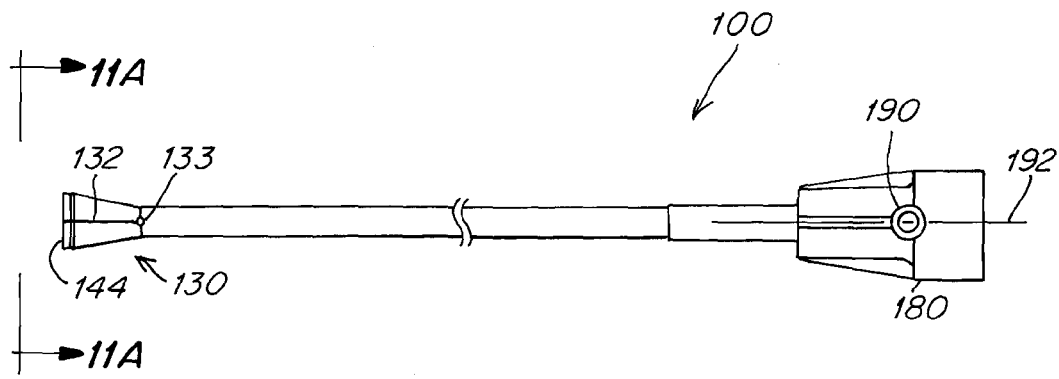
FIG. 11 is a side view of a sheath system according to one embodiment of the invention.
Figure 11A:
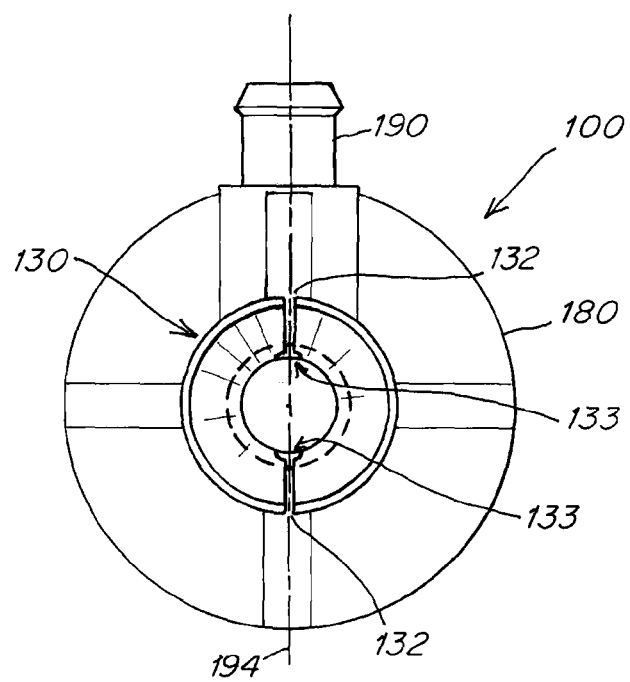
FIG. 11A is an end view of the sheath system of FIG. 11.

FIG. 11 shows another embodiment of sheath system 100 with slits 132 aligned with the proximal side port 190. The embodiment in FIG. 11 is shown in the expanded configuration. In this figure, the proximal side port 190 extends perpendicular to the plane of the page. Thus, the slits 132 and stress release ends 133 are radially aligned with a plane that extends perpendicular to the page and includes a central axis 192 of the sheath system 100 and the proximal side port 190 (this plane is shown in FIG. 11A). FIG. 11A is an end view along line 11A-11A of the embodiment of sheath system 100 shown in FIG. 11. As shown in FIG. 11A, a plane 194 passes through the central axis of the sheath system 100 and includes proximal side port 190 of proximal end 180. The figure illustrates how the slits 132 and stress release ends 133 of distal portion 130 fall within the plane 194. Thus, the slits 132 and stress release ends 133 of distal portion 130 are aligned with the proximal side port 190.

Therefore, the alignment between one of the slits 132 can be on the same side of the circumference of the inner sheath 120 as the proximal side port 190 (such as with the top slit 132), or the alignment can be on the opposite side of the circumference of the inner sheath 120, relative to the proximal side port 190 (such as with the bottom slit 132). In other words, although one of the slits 132 may be approximately 180° separated from the side port 190, the slit 132 and the side port 190 would be considered in alignment because they both fall in the plane 194 passing along the length of the inner sheath 120 and through the center of the inner sheath 120.

In certain embodiments, having the slits 132 and proximal side port 190 radially aligned provides for improved snag-resistance when used to retrieve an object. Similar advantages are thought to be achieved in embodiments with more than two slits by radially aligning the side port 190 with any one of the plurality of slits. In certain embodiments, the slits 132 are considered aligned with the side port 190 when the slits 132 are within 20° of the plane 194 that includes the side port 190. In other embodiments, the slits 132 are considered aligned with the side port 190 when the slits 132 are within 10° of the plane 194. In still further embodiments, the slits 132 are considered aligned with the side port 190 when the slits 132 are within 5° of the plane 194. However, the slits 132 need not be aligned with the side port 190 for the embodiments to function properly. Thus, the slits 132 and the side port 190 may have any orientation relative to one-another and be within the scope of the invention.

In at least one embodiment, the sheath system 100 is straight, extending from its proximal end to its distal end. In other embodiments, the sheath system 100 is curved, as illustrated in FIG. 12, to better suit a living body's anatomy. In the embodiment shown, a distal section 165 of the sheath system 100 is curved 35° away from an axis 175 defined by a proximal section 185 of the sheath system 100. Curves having greater or lesser angles are within the scope of the invention. Likewise, distal section 165 of the sheath system 100 may be curved in other ways known to those having ordinary skill in the art to be advantageous for deploying and/or retrieving implants and/or biological materials. For example, distal section 165 of the sheath system 100 can have a "J" curve, a Mullins curve, and a "hockey stick" curve. Furthermore, although not shown, the distal section 165 of the sheath system 100 may have a compound curve, that is, a curve in more than one plane (e.g., a Hausdorf-Lock curve). The specific shape and amount of curve of the distal section 165 of the sheath system 100 is determined, at least in part, by the intended use of sheath system 100 and the unique anatomy encountered.

In the embodiment shown in FIG. 12, the curve of the distal section 165 of the sheath system 100 is aligned with the slits 132 and stress release ends 133 (not shown). That is, the end of the sheath system shown in FIG. 12 curves in the plane of the page. The slits 132 and the stress release ends 133 also lie in the plane of the page (shown as plane 195 in FIG. 12A), and therefore, the curve, the slits 132, and the stress release ends 133 are aligned. FIG. 12A is an end view along line 12A-12A of the embodiment of sheath system 100 shown in FIG. 12. As shown in FIG. 12A, a plane 195 passes through the central axis of the sheath system 100 and includes both the distal section 165 (hidden behind distal portion 130) and the proximal section 165. The figure illustrates how the slits 132 and stress release ends 133 of distal portion 130 fall within the plane 195. Thus, the slits 132 and stress release ends 133 of distal portion 130 are aligned with the curve of the distal section 165.

The curved portion, the slits 132, and the stress release ends 133 may also optionally be aligned with the side port 190. In other words, the curve of the distal section 165 of the sheath system 100, the slits 132, the stress release ends 133, and the side port 190 all lie substantially in the plane 195. Although the alignment of these features is not required, it is thought to improve the snag-resistance of sheath system 100. In embodiments having more than one curve or a compound curve, the slits 132 and stress release ends 133 may, optionally, be aligned with the distal-most curve to obtain the improved snag-resistance.

As set forth above in connection with the alignment of the side port 190 and the slits 132, the curved portion can have any of the alignments recited above (e.g., within 20°, 10°, and 5°). The curved portion need not have a specific orientation in relation to the other features in order for the embodiments to function properly. Thus, the invention is not limited by the orientation of the curved portion, and all relative alignments are within the scope of the invention.

The sheath system 100 can be used with various types of retrieval systems, which pass through the sheath system 100 to access the interior anatomy of a patient. These retrieval systems engage a portion of the implant device to be removed from the patient. For example, the sheath system 100 can be used with the systems and techniques disclosed in U.S. patent application Ser. No. 11/070,027, entitled Delivery/Recovery System For Clover Leaf Septal Occluder, filed Mar. 2, 2005, incorporated by reference herein. That application taught a system including an inner catheter with claws disposed at the end of the inner catheter enveloped by an outer sheath. The claws are capable of grasping a partially or fully deployed implant device for withdrawing the device back into the outer sheath. The various embodiments of the sheath system 100 described herein can serve as the outer sheath to be used in combination with the inner catheter and claws elements set forth in the incorporated application. Thus, as the claws and inner catheter withdraw the implant device into the sheath system 100, the various elements described above cooperate to enable the implant to be withdrawn into the outer sheath with reduced snagging potential.

The retrieval systems that can be used with the embodiments of sheath system 100 are not limited to those described in the reference incorporated above. For example, the systems and techniques disclosed in U.S. patent application Ser. No. 11/235,661, entitled Occluder Device Double Securement System For Delivery/Recovery of Such Occluder Device, filed Sep. 26, 2005, incorporated by reference herein, can be used with the embodiments described above. Likewise, other systems and techniques, such as those known generally in the art, can be used with the systems and techniques disclosed herein.

Although various embodiments have been described in detail herein by way of illustration, it is understood that such detail is solely for that purpose and variation can be made by those skilled in the art without departing from the spirit and scope of the inventions.

What is claimed is:

1. A device for delivering or retrieving an object from a site within the body, comprising:
   an outer sleeve having a lumen; and
   an inner sheath having a proximal portion and a distal portion, the distal portion being disposed within the lumen, the distal portion having an unexpanded configuration and an expanded configuration, and the distal portion having a first distal inner diameter and a second proximal inner diameter, the first distal inner diameter being larger than the second proximal inner diameter when in the expanded configuration;
   wherein the outer sleeve overlays at least a portion of the distal portion of the inner sheath when the device is in use, and wherein the outer sleeve extends beyond at least a portion of the distal portion of the inner sheath to form an overhang; and
   wherein the distal portion of the inner sheath includes at least two axial slits extending proximally from a distal end of the distal portion, the axial slits forming flaps that collapse inward and overlap each other when the distal portion is in the unexpanded configuration.

2. A method of retrieving an object from a site within the body, comprising:
   engaging the object with a retrieval system;
   withdrawing the object proximally toward a sheath system, the sheath system including:
      an outer sleeve having a lumen; and
      an inner sheath having a proximal portion and a distal portion, the distal portion being disposed within the lumen, the distal portion having an unexpanded configuration and an expanded configuration, and the distal portion having a first distal inner diameter and a second proximal inner diameter, the first distal inner diameter being larger than the second proximal inner diameter when in the expanded configuration;
         wherein the outer sleeve overlays at least a portion of the distal portion of the inner sheath when the device is in use, and wherein the outer sleeve extends beyond at least a portion of the distal portion of the inner sheath to form an overhang; and
         wherein the distal portion of the inner sheath includes at least two axial slits extending proximally from a distal end of the distal portion, the axial slits forming flaps that collapse inward and overlap each other when the distal portion is in the unexpanded configuration;
   contacting the object with a distal edge of the distal portion;
   applying a withdrawing force on the object in the proximal direction so that the distal portion of the inner sheath slides over the object; and
   pulling the object past the distal edge and into the distal portion.

3. The method of claim 2, the distal portion further including a distal end, a proximal end, and a hinge disposed therebetween, and then applying the withdrawing force on the object causing at least a part of the distal end portion distal to the hinge to deflect inward or outward at the hinge relative to a central axis of the distal end portion.

4. The method of claim 2, further comprising contacting the object with a portion of the outer sleeve extending past a distal end of the inner sheath so that the outer sleeve portion centers the object relative to a lumen defined by the distal portion of the inner sheath.

* * * * *